United States Patent [19]

Krebs

[11] Patent Number: 5,445,168
[45] Date of Patent: Aug. 29, 1995

[54] METHOD FOR TREATING INTERUTERINE WALLS USING A RESECTOSCOPE

[76] Inventor: Helmut Krebs, 4849 N. Kenneth, Chicago, Ill. 60630

[21] Appl. No.: 156,250

[22] Filed: Nov. 22, 1993

Related U.S. Application Data

[63] Continuation of Ser. No. 8,680, Jan. 25, 1993, abandoned.

[51] Int. Cl.$^6$ ............................................. A61B 17/39
[52] U.S. Cl. .................................... 128/898; 606/46; 606/108
[58] Field of Search ............... 128/760, 761, 768, 830, 128/831, 833, 834, 837–841, 898, 3, 17–19; 604/328; 606/1, 108, 119, 45–50, 125, 126, 191–193

[56] References Cited

U.S. PATENT DOCUMENTS

| | | | |
|---|---|---|---|
| 4,606,336 | 8/1986 | Zeluff | 128/831 |
| 4,917,082 | 4/1990 | Grossi et al. | 606/46 |
| 5,188,122 | 2/1993 | Phipps et al. | 606/33 |
| 5,217,466 | 6/1993 | Hasson | 606/119 |
| 5,354,296 | 10/1994 | Turkel | 606/40 |

Primary Examiner—Stephen C. Pellegrino
Assistant Examiner—Glenn K. Dawson
Attorney, Agent, or Firm—Banner & Allegretti, Ltd.

[57] ABSTRACT

The method comprises inserting an interuterine sheath through a guide tube into the uterus of a patient, and then inserting the shaft of the resectoscope to a predetermined depth within the uterus. A medical procedure is performed with the resectoscope, such as scraping the interuterine walls. An irrigation liquid is charged into the uterus and then collected from the uterus, while being monitored in order to provide an indication of perforation of the interuterine wall. The method is completed by removing the resectoscope, interuterine sheath and guide tube from the patent.

8 Claims, 1 Drawing Sheet

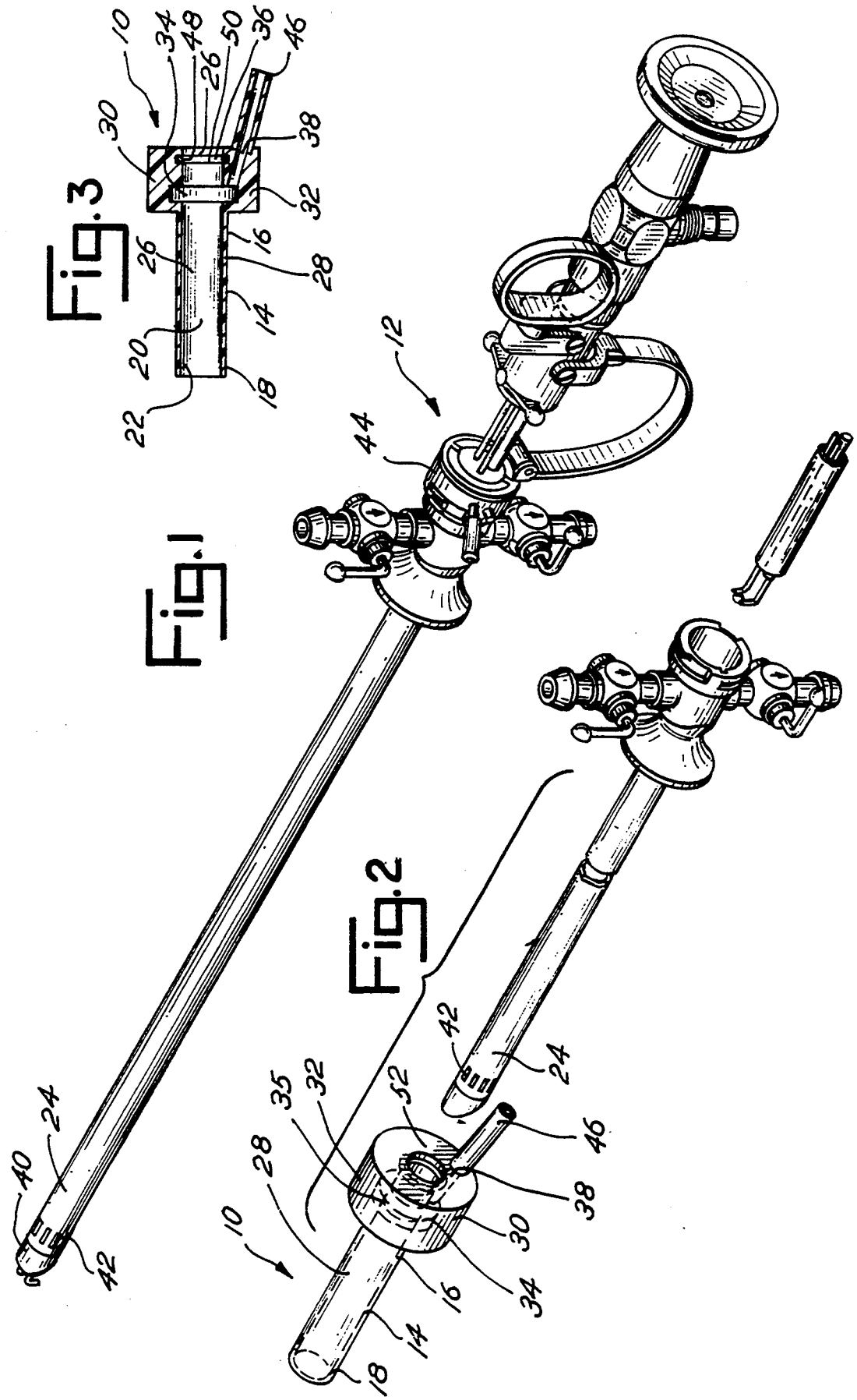

METHOD FOR TREATING INTERUTERINE WALLS USING A RESECTOSCOPE

This is a continuation of application Ser. No. 08/008,680, filed Jan. 25, 1993 now abandoned.

BACKGROUND OF THE INVENTION

The present invention is directed in general to insertion guides for medical instruments, and in particular to an interuterine sheath for insertion of medical instruments, such as hystoscopes into the uterus for providing various diagnostic and/or therapeutic procedures thereto.

In the prior art, a certain amount of longitudinally directed insertion force has been required to permit insertion of medical instruments through the internal diameter of the cervix and into the uterus. This required force is necessitated by reason of annularly disposed and gripping musculature within the cervix to urge the cervix into its normally closed (i.e., non-dilated) position. Accordingly, an initial amount of force has been necessary to penetrate the cervical opening with such medical instruments, such as the hystoscope. However, after such initial penetration, the amount of force necessary to slide the shaft of the medical instrument into the uterus is of a much lesser amount. In addition, the uterus is relatively short in its longitudinal dimension. Thus, the risk of perforation of the uterus wall during such insertion of a medical instrument is present.

Also, it is necessary to maintain a field of irrigation fluid within the uterus both for irrigation and visualization purposes. In prior art techniques, there were problems of fluid blockage of irrigation fluid ports on the hystoscope caused by the wall of the cervix. This also created a tendency for perforation of the uterus during movement of the instrument shaft to maintain flow of the irrigation fluid. The risk of perforation is also created in situations where the surgeon must move the treatment devices further into the uterus in order to facilitate perpendicularly evacuating fluid removal mechanisms to clear past the walls of the cervix.

In addition, the insertion guide of the present invention has a length which is not longer than that of the internal longitudinal dimension of the cervix, and thus will not extend the full length of the uterine cavity. As a result, when the invention is used for insertion into and thereby partial dilation of the cervix, there is no substantial danger created thereby of perforation of the uterus.

Accordingly, once the interuterine guide of the present invention is disposed into operative position within the cervix, the medical instrument can be inserted, removed and reinserted without substantial risk of perforation, because, inter alia, the need for redialation of the cervix during the course of the operation/surgery is eliminated.

Finally, with current devices, there is great difficulty in accounting for the volume of the irrigation fluid. However, with the structure of the present invention, all exiting fluids enter a central collection system, thus allowing the volume of the exiting irrigation fluid to be compared with the volume of the entering fluid, in order to determine the amount of loss of irrigation fluid into the body that may have occurred during the operation. With current systems, this function is not possible, because all of the exiting fluid does not enter a central collection and monitoring system.

By discharging irrigation fluid in a direction parallel to the longitudinal channel of the internal diameter of the cervix, the structure of the present invention also eliminates the prior art problems associated with blockage of the fluid removal path by the wall of the cervix. In addition, the structure of the present invention reduces the risks associated with cervical dilation (i.e., by holding the cervix in an operatively semi-dilated position, the structure hereof eliminates the need to re-dilate the cervix during operative procedures). In addition, these structures of the interuterine guide tube of the present invention allow for accountability of the irrigating fluid used during the course of an operation.

In addition to the above advantages, further advantages of the interuterine guide tube apparatus of the present invention will become known to those ordinarily skilled in the art upon review of the following summary of the invention, the brief description of the drawing, the detailed description of preferred embodiments, the appended claims, and the accompanying drawing.

SUMMARY OF INVENTION

The present invention is directed to a guide tube for facilitating insertion of medical instruments into a bodily cavity, and in preferred embodiments is directed to an interuterine guide tube for insertion into the cervix and thus partially within the uterus. The guide tube hereof holds the body cavity in an open and a partially dilated position allowing devices, such as medical diagnostic and/or treatment devices, to be inserted into the cavity through the opening in the guide tube sheath portion thereof. Any irrigation liquids or other fluids which may be irrigated within the cavity in a direction parallel to the dilation of the body opening may be exhausted or expelled therefrom. The guide tube hereof greatly reduces the risks associated with dilation and/or redialation of the body cavity, especially for example the cervix of the uterus. In addition, the guide tube apparatus hereof provides for accountability of irrigation fluids used during the course of a diagnostic or therapeutic treatment.

The inventive structure hereof exhausts irrigational fluids from the body cavity through an exhaust port located at an end thereof opposite to an insertion end. The inner diameter of the interuterine sheath of the present invention is larger than that of the various treatment device(s), thus allowing such treatment device(s) to be inserted through the interuterine sheath thereof and into the bodily cavity for treatment. The clearance between the abutting respective surfaces of the interuterine sheath and the treatment device(s) is to be sufficiently large to render the volume between the interuterine sheath and the treatment device(s) sufficiently large to exhaust fluid therebetween. Thus, the structures of the present invention remove irrigation fluids in a direction parallel to the longitudinal channel of the body cavity, thus eliminating the problems, such as blockage by the walls of the body cavity, that are associated with present day devices that attempt to remove fluid perpendicular to the body cavity. In addition, the unique structure of the present invention eliminates the need for liquid fluid removal mechanisms on the treatment devices, thus simplifying the structure of such devices and lowering over-all costs.

BRIEF DESCRIPTION OF THE DRAWING

The interuterine guide tube apparatus of the present invention is depicted in the accompanying drawing, and in which:

FIG. 1 is a perspective view of a resectoscope of the variety which may be utilized in association with the interuterine guide tube of the present invention;

FIG. 2 is a perspective view of the interuterine guide tube apparatus of the present invention showing the elongated interuterine sheath, which is connected to the cervical stop means disposed at the interuterine sheath, and further showing the fluid collection canal disposed obliquely to the elongated interuterine sheath, and further showing in exploded perspective as insertable therein the medical instrument of FIG. 1; and FIG. 3 is a longitudinal cross-sectional view of the interuterine guide tube apparatus guide invention, and shows the interior dimension of the interuterine sheath having an annular space for space fluid collection disposed near the proximal end thereof and having a sealing mechanism disposed downstream for preventing loss of irrigating fluid therefrom.

DETAILED DESCRIPTION OF PREFERRED EMBODIMENT

Operative hysteroscopy includes apparatus and methods for resecting, inter alia, submucous myomas, the symptoms of which may include menorrhagia, or may be otherwise detectible. One such presently utilized therapeutic medical procedure includes the use of a resectoscope, wherein a wire loop electrode or a two to three millimeter roller ball electrode is utilized operatively within the uterus. In such circumstances, the endometrium must be suppressed, according to medical techniques known to those ordinarily skilled in the art. The technology presently utilizable with such a resectoscope is relatively sophisticated, including ports thereon for permitting fluid output, for permitting fluid input, for directing to the operative field a light source (such as the fiberoptic) and other sensing means, including video camera and/or television attachment.

Nonetheless, despite such sophisticated equipment, multiple dilation of the cervical uterus and multiple reinsertions of such medical instruments therewithin has been necessitated. Such dilation and redialation in the case of uterine surgical procedures has been required because the medical operative instrument must be frequently removed for cleaning. Given the substantial danger level of uterine perforation which occurs during any finite number of such dialations, improvement is indicated in dilation and redialation structures, techniques and procedures. The improved inter-uterine guide apparatus of the present invention addresses that substantial problem in the prior art. In fact, in the broader scope of the present invention, the structure thereof may be utilized to facilitate insertion of other types of medical instruments into other body cavities, for example, where dilation and redialation constitute material difficulties and/or dangers.

Referring now to the drawing, wherein common numerals are utilized for common elements, the interuterine guide tube generally 10 of the present invention for facilitating insertion of a medical instrument generally 12 such as a hystoscope 44 within the uterine cervix, is depicted. An elongated interuterine sheath 14 having proximal and distal ends 16,18 is provided. The distal end 18 of the interuterine sheath 14 is inserted within the cervix of the uterus for disposition of a substantial portion of the interuterine sheath 14 within the uterus. The interuterine sheath 14 has a longitudinal dimension 20 which is less than the length of the uterus, and thus does not extend to the bottom of the uterus. The interuterine sheath 14 also has an internal diameter 22 which is slightly larger than shaft 24 of the corresponding medical instrument to provide an instrument passageway 26 which is substantially snug in fit with the operative portion of the medical instrument, such as the shaft 24 of the hystoscope 44 when inserted, but which will permit the exhaust flow of irrigating fluid along the longitudinal extent thereof. The interuterine sheath 14 also has an exterior diameter 28 which is smaller than the interior diameter of the penetrated semi-dilated uterus when such interuterine sheath 14 is inserted therewithin.

A cervical stop means 30 is disposed at the proximal end 16 of the interuterine sheath 14. Such stop means 30 may be in the form of a flange body 32. Such flange body 32 may contain a fluid collection chamber 35 and a fluid seal mechanism 36 for the shaft 24 of the medical instrument 44 to prevent leakage of exhausting irrigation fluid therefrom. The cervical stop means 30 limits the depth of insertion of the interuterine sheath 14 into the uterus and also facilitates withdrawal of the interuterine sheath from the partially dilated uterus at the close of the diagnostic and/or operative procedure. Such cervical stop means 30 has a transverse dimension which is necessarily larger than the diameter of the cervix and may be in the shape, for example, of a tube of relatively low height. The irrigation fluid collection chamber 38 and associated effluent channel for exhausting irrigation fluid of the uterine insertion guide tube of the present invention is connected with the internal diameter 22 of the interuterine sheath 14 for receipt of irrigation fluid emanating from the uterus. Such effluent fluid may be in the form of irrigation liquid which is injected within the uterus by ports 42 disposed at the distal portion 40 of the medical instrument 12 to provide a constantly flowing irrigation field within the uterus, inter alia, for the purpose of flushing away any debris removed from the uterus by the surgical instrument, and also to provide a clear and transparent operative field for the light emitting photoscopic mechanism disposed at the distal end of the medical instrument, such as a hystoscope 44. In addition, by monitoring the amount of such irrigating fluid discharging from the uterus and comparing such discharge volume with the amount of irrigating fluid charged to the uterus, the possibility of a uterine perforation can be detected by these means.

The uterine insertion guide tube 10 of the present invention further includes a fluid seal mechanism 36 which may in some preferred embodiments be disposed at the inner diameter 22 of the interuterine sheath 14 and proximally of the fluid connection chamber 28 for preventing discharge of fluid from the uterus through the proximal end 16 of the uterine sheath 14. As set forth in the figures hereof, the internal diameter 22 of the interuterine sheath 14 is preferably cylindrically shaped, (and in any event takes the shape of the medical instrument to be inserted therewithin). Such cylindrical shape permits a substantially snug fit and also allows for any rotation of shaft 24 of the medical instrument which may be required. The interuterine sheath 14 also preferably has a cylindrically shaped exterior diameter 28 to match the basic shape of a partially dilated cervix, and to permit gripping of the exterior diameter 28 of the interuterine sheath 14 by the muscles annularly disposed about the uterine cervix. Such fluid collection means in preferred embodiments includes a fluid annular space 34 disposed about the instrument passageway 26, and disposed within the flanged body 32. Such fluid annular space 34 functions for annularly collecting the uterine discharge irrigation fluid emanating from the uterus. In preferred embodiments, a fluid discharge tube 46 is connected to the fluid annular space 34 for channeling the uterine discharge therethrough. The fluid discharge tube 46 or channel may be disposed obliquely to the longitudinal dimension of the interuterine guide tube 14.

In addition to the above mechanisms, the fluid collection means further comprises irrigation fluid collection means for receipt of irrigation fluid charged to the uterus by means of the medical instrument.

The preferred embodiments of the fluid seal mechanism comprises preferably an O-ring 48 disposed within an annular groove 50, although of course alternative sealing mechanisms known to those skilled in the art may be used. Such O-ring groove 48 is annularly disposed about the internal diameter 22 of the interuterine sheath 14, and is disposed yet proximally of the fluid collection chamber 35 in order to prevent leakage of fluid from the proximal end 16 of the interuterine sheath 14 where the medical instrument 12 is inserted therewithin.

Fluid monitoring means of the type known to those skilled in the art may be connected with the fluid collection means for measuring the amount of uterine discharge irrigation fluid. Such fluid monitoring means may also include means for comparing the volume of the uterine discharge irrigation fluid with the amount of fluid charged to the uterus in order to detect the possibility of uterine perforation. These means may include electronic comparison means to provide an alarm signal indicating the possibility of uterine perforation. Such fluid comparative and electronic means are known to those of ordinary skill within the relevant arts.

What is claimed is:

1. An improved method of facilitating insertion of a shaft of a resectoscope within a human uterus having a uterus passageway therein and interuterine walls, said method comprising:

providing a uterine guide tube having an elongated interuterine sheath having a longitudinal dimension and proximal and distal ends, and futher having a resectoscope passageway which has an internal dimension slightly larger than the shaft of the resectoscope;

inserting the distal end of the interuterine sheath into the uterus to a depth substantially less than the length of the uterus;

inserting the shaft of the resectoscope in a first direction within the resectoscope and to a predetermined depth within the uterus which is less than the length of the uterus passageway;

performing a medical procedure within the uterus and upon the interuterine walls by means of the resectoscope;

charging an irrigation liquid through the interuterine sheath into the uterus while performing the medical procedure;

collecting the irrigation liquid from the uterus and discharging the collected irrigation liquid from the interuterine sheath monitoring the amount of irrigation liquid charged to and collected from the uterus;

removing the resectoscope from the uterus by sliding the shaft of the resectoscope within the interuterine sheath in a second direction which is opposite to the first direction; and removing the uterine guide tube from the uterus.

2. The improved method of claim 1 further comprising the steps of re-inserting the shaft of the resectoscope within and re-removing the shaft of the resectoscope from the interuterine sheath at least once prior to removing the uterine guide tube from the uterus.

3. The improved method of claim 1 further comprising providing cervical stop means at the proximal end of the interuterine sheath and limiting thereby the depth of insertion of the interuterine sheath within the uterus to a depth substantially less than the full length of the uterus.

4. The improved method of claim 3 wherein said provided cervical stop means comprises a flange body.

5. The improved method of claim 1 further comprising comparing the volume of the irrigation liquid charged to and collected from the uterus in order to detect the possibility of a uterine perforation.

6. The improved method of claim 1 wherein said resectoscope includes a wire loop electrode.

7. The improved method of claim 1 wherein said resectoscope includes a roller ball electrode.

8. The improved method of claim 1 wherein said medical procedure performed upon the interuterine walls by means of the resectoscope comprises resecting a submucous myoma.

* * * * *